(12) United States Patent
Sonderegger, Sr.

(10) Patent No.: US 11,305,058 B2
(45) Date of Patent: Apr. 19, 2022

(54) INFUSION BUMP CAPTURE NEEDLE SHIELD

(71) Applicant: Becton, Dickinson and Company, Franklin Lakes, NJ (US)

(72) Inventor: Ralph L. Sonderegger, Sr., Farmington, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 513 days.

(21) Appl. No.: 16/320,372

(22) PCT Filed: Jul. 20, 2017

(86) PCT No.: PCT/US2017/043138
§ 371 (c)(1),
(2) Date: Jan. 24, 2019

(87) PCT Pub. No.: WO2018/022432
PCT Pub. Date: Feb. 1, 2018

(65) Prior Publication Data
US 2020/0023124 A1    Jan. 23, 2020

Related U.S. Application Data

(60) Provisional application No. 62/367,391, filed on Jul. 27, 2016.

(51) Int. Cl.
*A61M 5/158* (2006.01)
*A61M 25/06* (2006.01)

(52) U.S. Cl.
CPC ........ *A61M 5/158* (2013.01); *A61M 25/0612* (2013.01); *A61M 25/0618* (2013.01); *A61M 25/0631* (2013.01); *A61M 2005/1585* (2013.01); *A61M 2005/1586* (2013.01); *A61M 2005/1587* (2013.01)

(58) Field of Classification Search
CPC .......... A61M 5/158; A61M 2005/1585; A61M 2005/1586; A61M 2005/1587;
(Continued)

(56) References Cited

U.S. PATENT DOCUMENTS 6,749,588 B1 * 6/2004 Howell ............... A61M 5/3273
604/110
2002/0169418 A1    11/2002 Menzi et al.
(Continued)

FOREIGN PATENT DOCUMENTS

CN       101909681 A    12/2010
ES         1067206 U     5/2008
(Continued)

OTHER PUBLICATIONS

Japanese Office Action dated Apr. 27, 2021, which issued in the corresponding Japanese Patent Application No. 2019-504111, including English translation.
(Continued)

*Primary Examiner* — Theodore J Stigell
(74) *Attorney, Agent, or Firm* — Dickinson Wright PLLC

(57) ABSTRACT

An infusion device includes a base for removably coupling to a fluid deliver device, a needle hub supporting an introducer needle and a catheter for delivering a substance to a patient. The infusion device includes a needle shield for covering the introducer needle after inserting the catheter into the patient. The needle shield includes a leg with a latching tab to couple to the coupling of the base until the legs spring outward to release the coupling. The legs have inwardly extending overlapping arms with an aperture receiving the introducer needle. A spring guard is formed on the needle shield and is spring biased inwardly toward the introducer needle to contact the arms. The introducer needle is retracted to release the arms allowing the arms to spring (Continued)

outwardly to disengage from the coupling of the base and to enable spring guard to spring inwardly to cover the tip of the introducer needle.

22 Claims, 17 Drawing Sheets

(58) Field of Classification Search
CPC .. A61M 5/3273; A61M 5/329; A61M 5/3219; A61M 2005/14256; A61M 25/0612; A61M 25/0618; A61M 25/0631
See application file for complete search history.

(56) References Cited

U.S. PATENT DOCUMENTS

| | | |
|---|---|---|
| 2007/0191771 A1 | 8/2007 | Moyer |
| 2012/0220956 A1 | 8/2012 | Kuracina et al. |
| 2014/0221939 A1 | 8/2014 | Woehr et al. |
| 2014/0316379 A1 | 10/2014 | Sonderegger et al. |
| 2015/0196737 A1 | 7/2015 | Baid |
| 2016/0354539 A1 | 12/2016 | Tan et al. |

FOREIGN PATENT DOCUMENTS

| | | |
|---|---|---|
| JP | 2002-325847 A | 11/2002 |
| JP | 2007-521918 A | 8/2007 |
| WO | 2005/079891 A1 | 1/2005 |
| WO | 2005/042073 A1 | 5/2005 |

OTHER PUBLICATIONS

International Search Report dated Oct. 5, 2017, which issued in the corresponding PCT Patent Application No. PCT/US2017/043138.
Chinese Office Action dated Dec. 31, 2020, which issued in the corresponding Chinese Patent Application No. 201710614711.1, including Eng. translation.

* cited by examiner

INFUSION BUMP CAPTURE NEEDLE SHIELD

This application claims priority under 35 U.S.C. § 119(e) from U.S. Provisional Application Ser. No. 62/367,391, filed on Jul. 27, 2016, which is incorporated herein by reference in its entirety.

FIELD OF THE INVENTION

The present invention relates generally to infusion devices, and more particularly, to subcutaneous infusion devices to be used in conjunction with an infusion pump in the infusion of insulin and other medicaments. The invention also relates to a catheter and introducer needle assembly that includes a needle shield that will safely shield the distal end of the introducer needle after the needle has been used to insert the catheter into a patient. The needle shield is constructed to disengage from the coupling of the infusion device after the introducer needle is withdrawn from the catheter.

BACKGROUND OF THE INVENTION

One mode of insulin infusion treatment includes infusion pump therapy via a catheter, needle or other type of cannula. Infusion pumps have the advantage of continuous infusion of insulin, precision dosing, and programmable delivery schedules. These advantages result in more accurate blood glucose control. In this mode of insulin infusion treatment, the infusion pump remains attached to the user and required doses of insulin are delivered to the user via the pump.

One type of cannula is a catheter, which generally is a tube that can be inserted into the body to permit the administration of fluids. In infusion pump therapy, the types and sizes of the catheter may vary, but generally, the catheter is a thin, flexible tube. In some uses, however, it may be larger and/or rigid. A rigid, hollow, metal needle may also be used in place of a soft plastic catheter.

One type of conventional infusion device, known as an infusion set, includes a catheter assembly connected to a pump by a tubing set, and a separate insertion device inserts and/or attaches the catheter assembly into/to a user via an introducer needle provided as part of the infusion device. The infusion device and insertion device can also be combined into one unit.

Another type of insulin infusion device, known as a "patch pump," has recently become available. Unlike a conventional infusion pump, a patch pump is an integrated device that combines most or all of the fluid components in a single housing that is adhesively attached to an infusion site, and does not require the use of a separate tubing set. A patch pump adheres to the skin, contains insulin (or other medication), and delivers the drug over a period of time, either transdermal, or via an integrated subcutaneous mini-catheter. Some patch pumps communicate with a separate controller device wirelessly (such as one sold under the brand name OmniPod®), while others are completely self-contained.

A conventional infusion device can include a fluid connector, which may be releasably attached to a base that can be secured to a user's skin. An infusion pump supplies fluid to a catheter via the fluid connector/base engagement.

Additionally, to protect the cannula and/or introducer needle prior to insertion, conventional devices often include a needle guard that is removed prior to use. These needle guards, however, are often very small and may be difficult to grasp, particularly for people with impaired dexterity. Additionally, conventional needle guards are often held in place by friction alone. To remove such needle guards, patients must pull and/or twist the needle guard, and the axial force required to remove such needle guards may vary widely, for example, based on manufacturing tolerances. Further, with such needle guards, once the coefficient of static friction is overcome, the guard may separate quickly, without providing an opportunity for a user to modify the applied force and potentially resulting in a needle-stick injury. Further, there is a risk that the needle guard can contact the needle during removal, potentially dulling the cannula or introducer needle.

The introducer needle after use is normally discarded. To prevent needle stick from the introducer needle a shield is provided to cover the introducer needle. Various needle shields have been developed to cover the needle after use. Some needle shields are bulky, difficult to use, required particular features or techniques to operate or can leave the sharp end exposed.

Some of these needle shields can be easily disconnected from the catheter hub before the needle shield covers the sharp distal tip of the introducer needle. One mechanism to avoid premature disconnection includes a plurality of fingers longitudinally extending from the needle shield with tabs extending radially inwardly from the fingers that engage the flange at the proximal end of the catheter hub. The fingers and tabs hold the needle shield to the catheter. The configuration of the fingers and tabs is designed such that the force needed to overcome the engagement between the fingers and tabs and the catheter hub is greater than the typical force needed to move the introducer needle proximally into the needle shield. Once the introducer needle has been fully withdrawn into the needle shield, a greater force can be applied to remove the needle shield from the catheter hub. The needle shield remains engaged with the catheter until the introducer needle has been completely removed from the catheter and is safely shielded in the needle shield. This configuration does not consistently ensure that the needle shield remains connected to the catheter hub until the introducer needle is locked in the needle shield. This may be undesirable because the contaminated needle could then be exposed increasing the chances for an accidental needle-stick.

The prior devices are generally suitable for the intended purpose. However, there is a continuing need for an improved needle shield that will protect the user from accidental needlestick.

SUMMARY OF THE INVENTION

One object of embodiments of the present invention is to substantially address the above and other concerns, and provide improved infusion devices. Another object of embodiments of the present invention is to provide an infusion device having a needle hub assembly with a needle shield.

These and other objects are substantially achieved by providing an infusion device, including a base having a distal side for attaching to a patient at an infusion site, a fluid connector that can be removably coupled to the base, and a needle hub assembly. The needle hub assembly includes a needle hub having a moveable needle shield for covering an insertion needle after removing from the base. The base includes a base section extending proximally from a surface of the base, with a coupling for connecting to the fluid connector. The needle hub supports an insertion needle that extends through a catheter coupled to the base for the insertion of the catheter into the patient. A needle shield slides within the needle hub during the separation of the needle hub from the base to cover the tip of the insertion needle to prevent injury to the patient.

The needle hub assembly of the invention includes a connection end for connecting to the base of the infusion device for insertion of the insertion needle and catheter into the patient. The needle hub assembly has a needle shield for sliding to an extended position after insertion to slide over the insertion needle. The needle hub slides over the needle shield by pulling upward on the needle hub to retract the insertion needle from the catheter into the needle shield. The needle hub in the operating position engages the needle shield to prevent the needle shield from separating from the base. Sliding the needle hub to a position where the needle shield is in an extended position enables the needle shield to separate from the base and cover the end of the needle.

The needle shield in one embodiment of the invention includes a spring member having at least two legs that are spring biased outwardly from the axis of the introducer needle and a spring guard that is biased inwardly toward the needle to cover the end of the introducer needle. The legs can have decent, hook or latch that can couple to the coupling of the needle hub to inhibit separation or sliding movement of the needle hub relative the base. The legs can be disengaged from the needle hub whereby the needle hub can slide upward with respect the needle shield. In one embodiment, the legs are flexible and spring away from the introducer needle when the introducer needle hub is retracted into the needle hub.

The needle shield of the invention can be a one piece spring member having two legs that are configured for connecting with the coupling of the base of the infusion device and a spring clip that is able to move or pivot over the tip of the introducer needle when deployed. The needle shield is retained within the needle hub during insertion of the needle and catheter into the patient. The needle hub is pulled from the base when the introducer needle and introducer needle are retracted from the base and catheter of the infusion device. As the needle hub and introducer needle are retracted, the introducer needle separates from the legs of the needle shield to allow the legs to spring outwardly to disengage the base and the spring guard moves toward the axis of the introducer needle over the tip to prevent accidental injury to the patient.

These and other objects are also substantially achieved by providing an infusion device comprising a base, a needle hub and a needle shield. The base includes a catheter and a coupling for connecting to a delivery device for supplying a drug or medication to the patient. The needle hub has an introducer needle fixed to the needle hub that extends from the needle hub and through the catheter. The introducer needle has a proximal end coupled to the needle hub and a distal end, where the introducer needle extends through an axial passage of said catheter. The needle shield is received in the needle hub and is able to slide with respect to the needle hub. The needle shield has a proximal end and a distal end, where the distal end has two legs for coupling to a coupling the base when the introducer needle is in contact with said legs and the needle shield is received said needle hub. When the needle shield is withdrawn from the needle hub and the introducer needle is withdrawn and separated from the legs, the legs spring bias outwardly and disengage the coupling of said base.

The features of the invention are further attained by providing an infusion device comprising a base, a needle hub and a needle shield. The base includes a catheter and a coupling for connecting to a delivery device for supplying a drug or medication to the patient. The needle hub has an introducer needle fixed to the needle hub that extends from the hub and through the catheter. The needle hub has a bottom end for contacting the base. The needle shield is received in the needle hub for sliding with respect to the needle hub from a first retracted position to a second extended position where the shield can cover the tip of the insertion needle. The needle shield has at least two legs for connecting to the coupling of the base. The legs can be released or unlatched from the needle hub by sliding the needle hub upward relative to the base and the needle shield thereby allowing separation of the needle shield from the base.

The advantages of the invention are further attained by providing a base having a catheter and a coupling configured for connecting to a delivery device, a needle hub and a needle shield. The needle hub has a recess at an open end, and an introducer needle positioned within the recess with a proximal end coupled to the needle hub and a distal end for extending through as axial passage of said catheter. The needle shield is removably received in the recess of the needle hub. The needle shield has two outwardly biased legs having a distal end for coupling with the needle hub in a first position and an arm for contacting said introducer needle, and a spring guard biased toward the insertion needle and the arms of the legs, where the introducer needle in a first position contacts the arms to retain the legs in coupling engagement with the needle hub and where the introducer needle is in a second position and the needle shield is withdrawn from the recess of the needle hub. The legs bias outwardly to a second position to disengage from the needle hub and the spring guard is biased to a position over the distal end of the introducer needle.

The features of the invention are further attained by proving an insertion needle hub assembly comprising a needle hub and a needle shield. The needle hub has an introducer needle with a proximal end coupled to the needle hub and a distal end. The introducer needle is configured for extending through a catheter of an infusion device. The needle shield has a proximal end and a distal end where the distal end has two legs biased away from each other. Each leg has an arm contacting the insertion needle, and a spring guard configured to flex between a first position and a second position and biased in a direction substantially perpendicular to a longitudinal axis of the insertion needle. The distal end of the introducer needle engages the legs. The spring contacts the legs and is retained in the first position. When the introducer needle is withdrawn to disengage the legs, the spring guard is biased to the second position over the distal end of the introducer needle.

These and additional aspects and advantages of the present invention will be set forth in the description that follows, or will be apparent from the description, or may be learned by practice of the invention.

BRIEF DESCRIPTION OF THE DRAWINGS

The various objects, advantages and novel features of the exemplary embodiments of the present invention will be more readily appreciated from the following detailed description when read in conjunction with the accompanying drawings, in which.

DETAILED DESCRIPTION OF EXEMPLARY EMBODIMENTS

Figure 1:
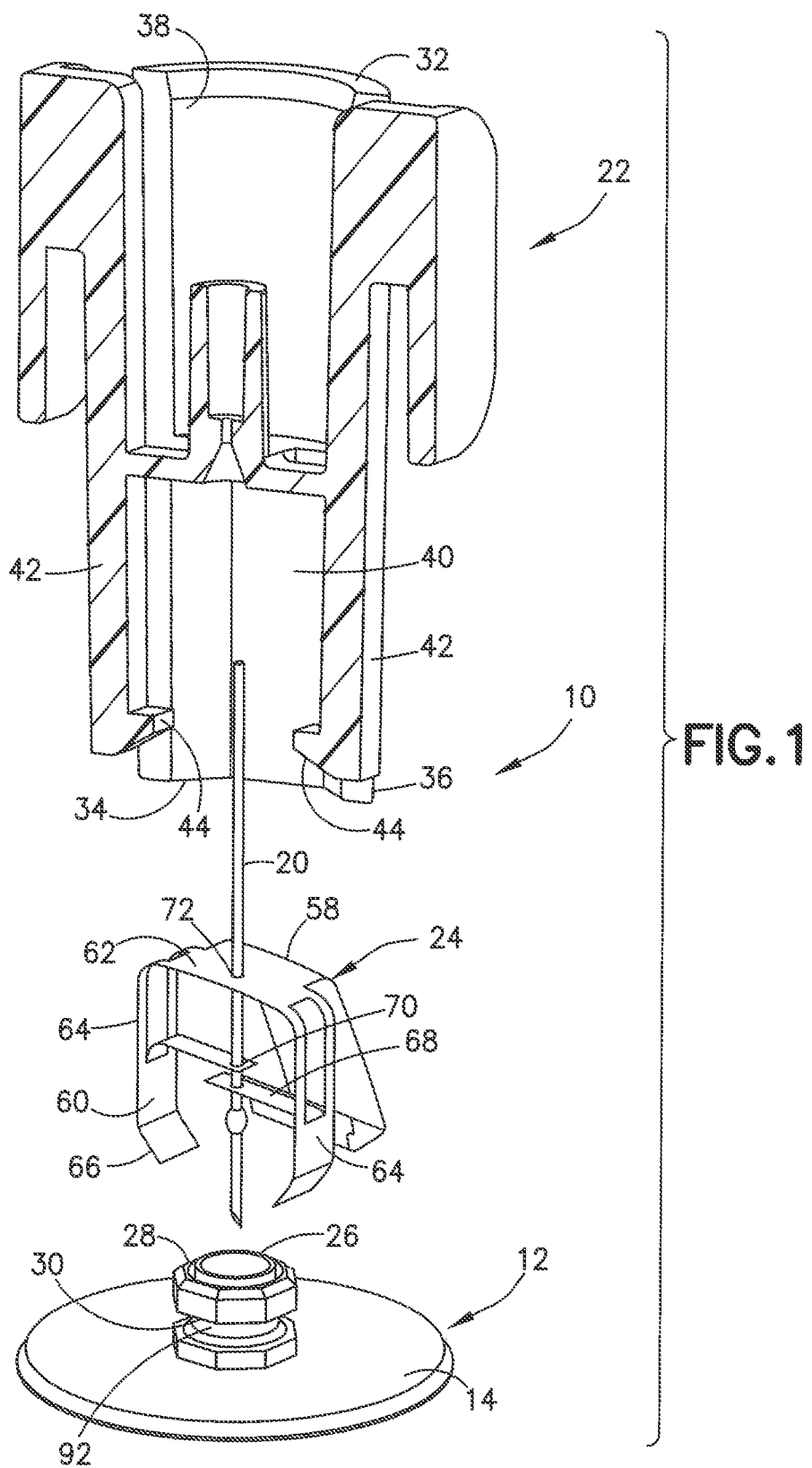
FIG. 1 is a perspective exploded view of a needle hub assembly connected to an infusion device base in accordance with an exemplary embodiment of the present invention.

Reference will now be made in detail to an embodiment of the present invention, which is illustrated in the accompanying drawings, wherein like reference numerals refer to like elements throughout. The embodiment described herein exemplifies, but does not limit, the present invention by referring to the drawings. As will be understood by one skilled in the art, terms such as up, down, bottom, top, proximal, and distal are relative, and are employed to aid illustration, but are not limiting.

Figure 2:
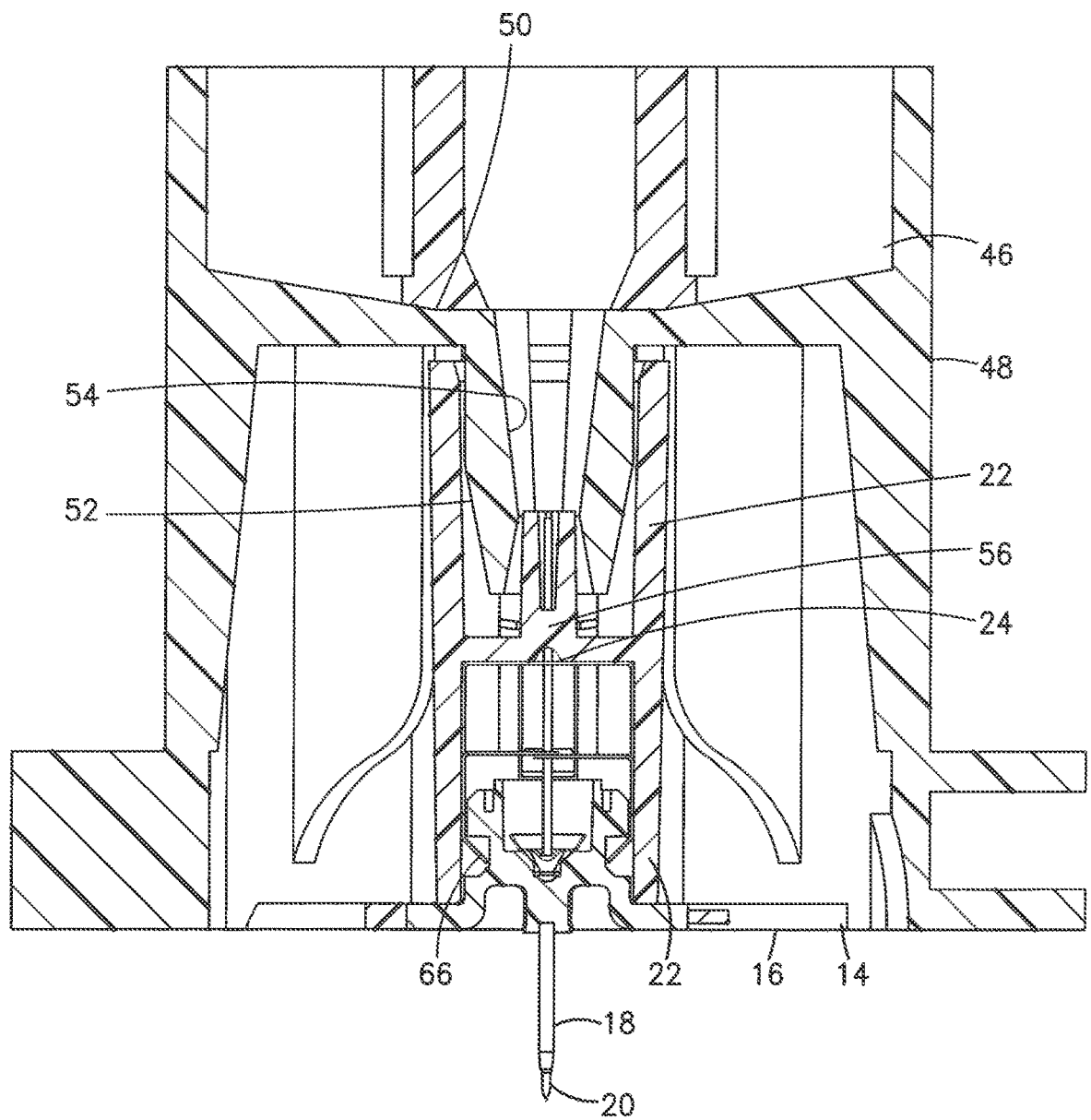
FIG. 2 is a cross-sectional view the needle hub assembly and base in an embodiment of invention.

FIG. 1 illustrates an exemplary embodiment of an infusion device, in this case an infusion set, including an introducer needle hub assembly 10 engaged with a base 12. Base 12 engages a flexible disc 14 providing improved comfort and mobility of the device because it moves with the user during physical activity while minimizing contact of the rigid portions of base 12 with the user. Flexible disc 14 has an adhesive patch or pad 16 with an adhesive backing to secure base 12 to the user's skin as shown in FIG. 2. FIG. 1 is a perspective view of hub assembly 10 disconnected from base 12 of the infusion device in one embodiment of the invention. Base 12 has mushroom shaped coupling 26 for connecting to a fluid delivery device of an infusion device as known in the art. Mushroom shaped coupling 26 has a top end 28 formed by the undercut edge 30 for connecting to the delivery device and for connecting to the needle hub during insertion of the catheter into the patient.

Figure 4:
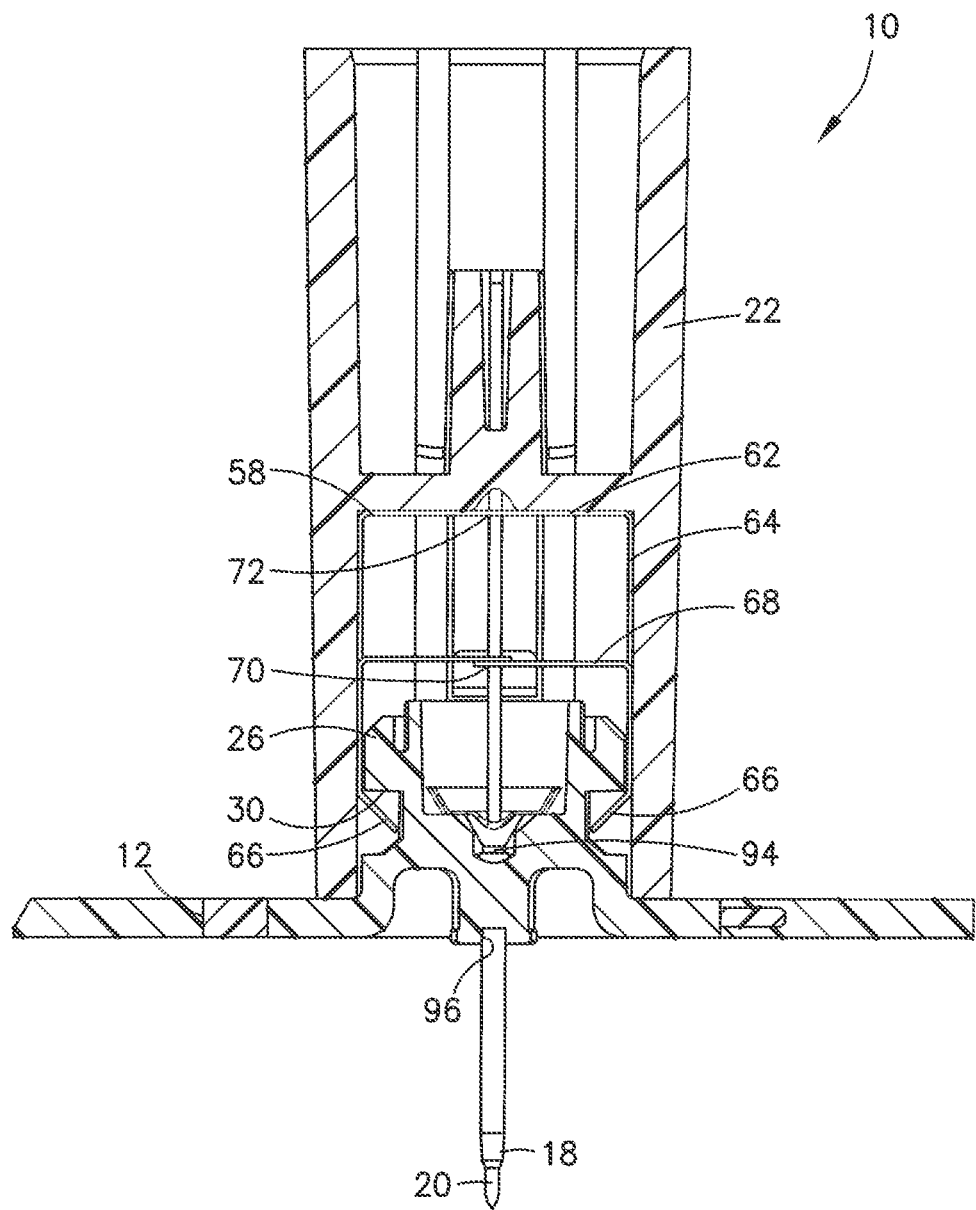
FIG. 4 is a cross-sectional side view of the needle hub and needle shield of FIG. 2 showing the needle shield connected to the coupling of the base.

Referring to FIG. 1 and FIG. 2, needle hub 22 has a substantially cylindrical shape with an open top end 32 and an open bottom end 34. Open top end 32 is defined by a side wall 36 forming a substantially cylindrical recess 38. Side wall 36 further defines a substantially cylindrical recess 40 in open bottom end 34. The bottom of the side wall is formed with flexible legs 42 having an inwardly extending hook 44 for connecting with the undercut 30 of the coupling of the base as shown in FIG. 4. Flexible legs 42 grip coupling 26 to resist separation until a sufficient upward force is applied to separate the needle hub from the coupling.

Needle hub assembly 10 is constructed to cooperate with an insertion device 46 shown in FIG. 2 for applying a downward force to the assembly 10 for inserting insertion needle 20 and catheter 18 into the patient. As shown in FIG. 2, insertion device 46 has a cylindrical shape to complement the outer dimension of needle hub 22 and base 12 for applying a downward pressure on the hub assembly during insertion to the patient. In the embodiment shown, insertion device 46 has a side wall 48 forming a cavity to receive the hub assembly 10 and a top wall 50 with a projecting member 52 to engage the open end of the needle hub 22. In one embodiment projecting member 52 of the insertion device 46 has an axial bore 54 for mating with needle hub 22 by a friction fit. Examples of insertion devices are known in the art for assisting in the insertion of an infusion device into the skin of a patient.

FIG. 2 illustrates the introducer needle hub assembly 10 and base 12 in a position where a soft (flexible) catheter 18 and an introducer needle 20 can be introduced into the patient. FIG. 2 is a cross-sectional view of the base 12 and introducer needle hub assembly 10 shown in FIG. 1.

An introducer needle 20 is fixed to a needle mounting structure 56 of needle hub 22 to fix introducer needle 20 against axial movement relative to needle hub 22. Needle hub 22 is used to insert introducer needle 20 and catheter 18 into the patient without requiring the user to hold or manipulate introducer needle 20 directly. Introducer needle 20 can be a hollow or solid stainless steel needle with a sharp beveled distal end. As shown, introducer needle 20 has a length to extend from the distal end of catheter 18 a distance to enable penetration into the skin to insert the catheter 18 to a desired depth.

Figure 9:
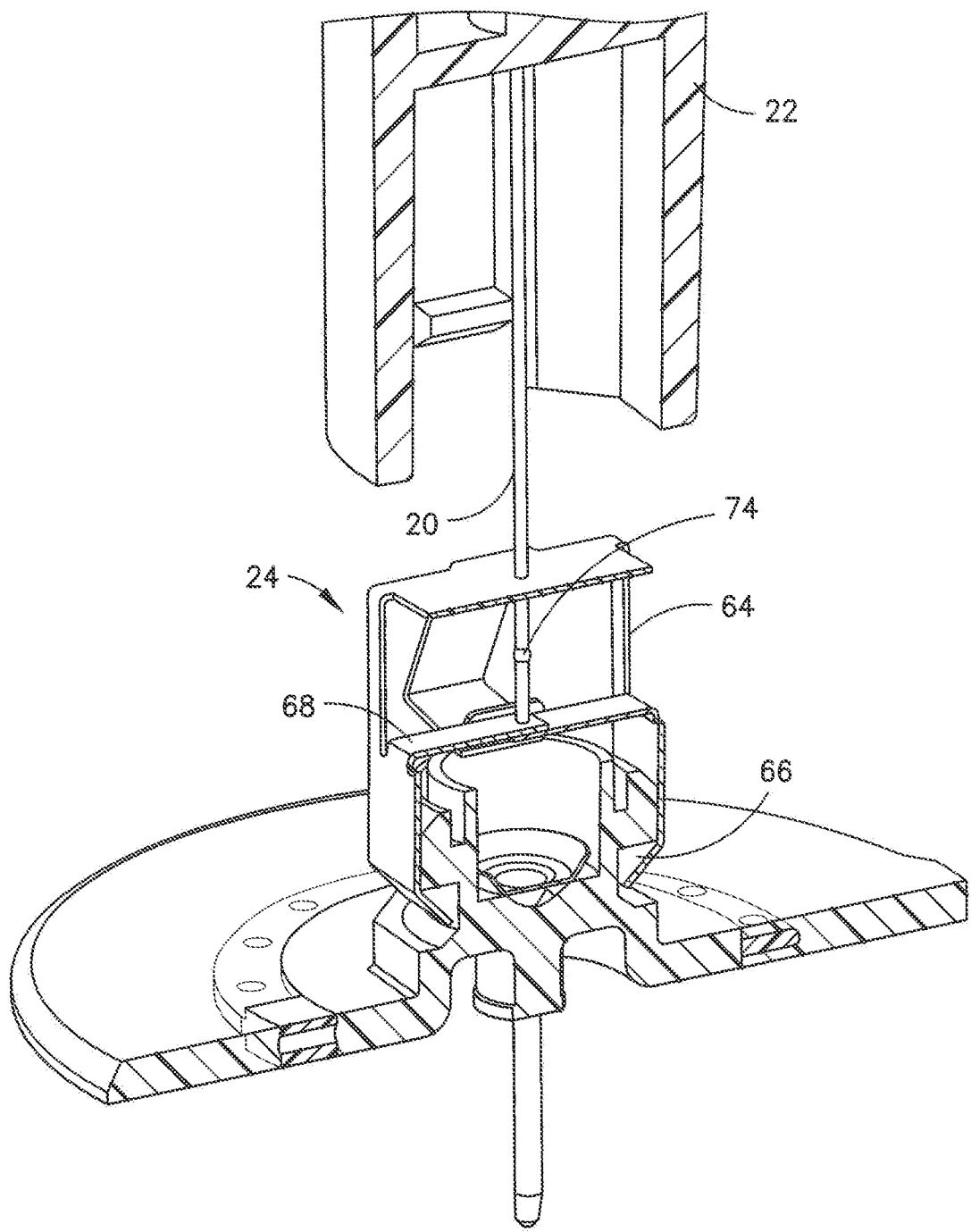
FIG. 9 is a perspective view showing the needle hub separated from the needle shield and coupling of the base before release of the needle shield from the coupling of the base.

Needle shield 24 has a shape to slide within the side wall of needle hub 22 between a first position received in the needle hub in the position shown in FIG. 2 and extended position shown in FIG. 9 where inserter needle 20 is retracted within the needle shield 24. Needle shield 24 includes a proximal end 58 received in needle hub 22 in a starting position and a distal end for connecting to the base 12. Needle shield 24 in the embodiment shown is a one piece, spring member formed from spring steel or other resilient material.

Needle shield 24 includes a body 62 with two legs 64 extending from the body in an axial direction. Each leg 64 has an inwardly extending latching tab member 66 for engaging coupling member 26 of base 12 to retain needle shield 24 on base 12 during insertion of introducer needle 20 and catheter 18 into the patient. In the embodiment shown, latching tab member 66 is an angled end portion of leg 64 that is bent inwardly toward the axis of needle hub 22 at an angle to grip the undercut 30 forming a bottom surface of mushroom shaped coupling 26 of base 12.

In the embodiment shown, legs 64 of needle shield 24 extend in an axial direction with respect to introducer needle 20. The legs 64 include an inwardly extending arm 68 that is cut or punched from the legs 64 as shown in FIG. 1. The arms 68 extend inwardly toward the center longitudinal axis of the introducer needle 20 and have a length so that the ends overlap each other. Each arm 68 has an aperture 70 that when aligned receives introducer needle 20 to retain the legs 64 in a first retracted position where latching tab members 66 are able to grip mushroom shaped coupling member 26 of base 12 and resist separation of the needle shield 24 from coupling member 26. The legs 64 are spring biased outwardly from the center axis of needle shield 24 in opposite directions away from introducer needle 20 so that when the introducer needle is withdrawn from apertures 70, legs 64 spring outward to separate from coupling 26.

Body 62 includes an aperture 72 for receiving the introducer needle 20 where introducer needle 20 can slide within the aperture. As shown in FIG. 1, introducer needle 20 has a bump 74 projecting outwardly from the outer surface of introducer needle 20. Bump 74 has a substantially spherical shape with an outer dimension greater than the inner dimension aperture 72 so that introducer needle 20 can slide within aperture 72 but retains needle shield 24 on introducer needle 20.

Figure 5:
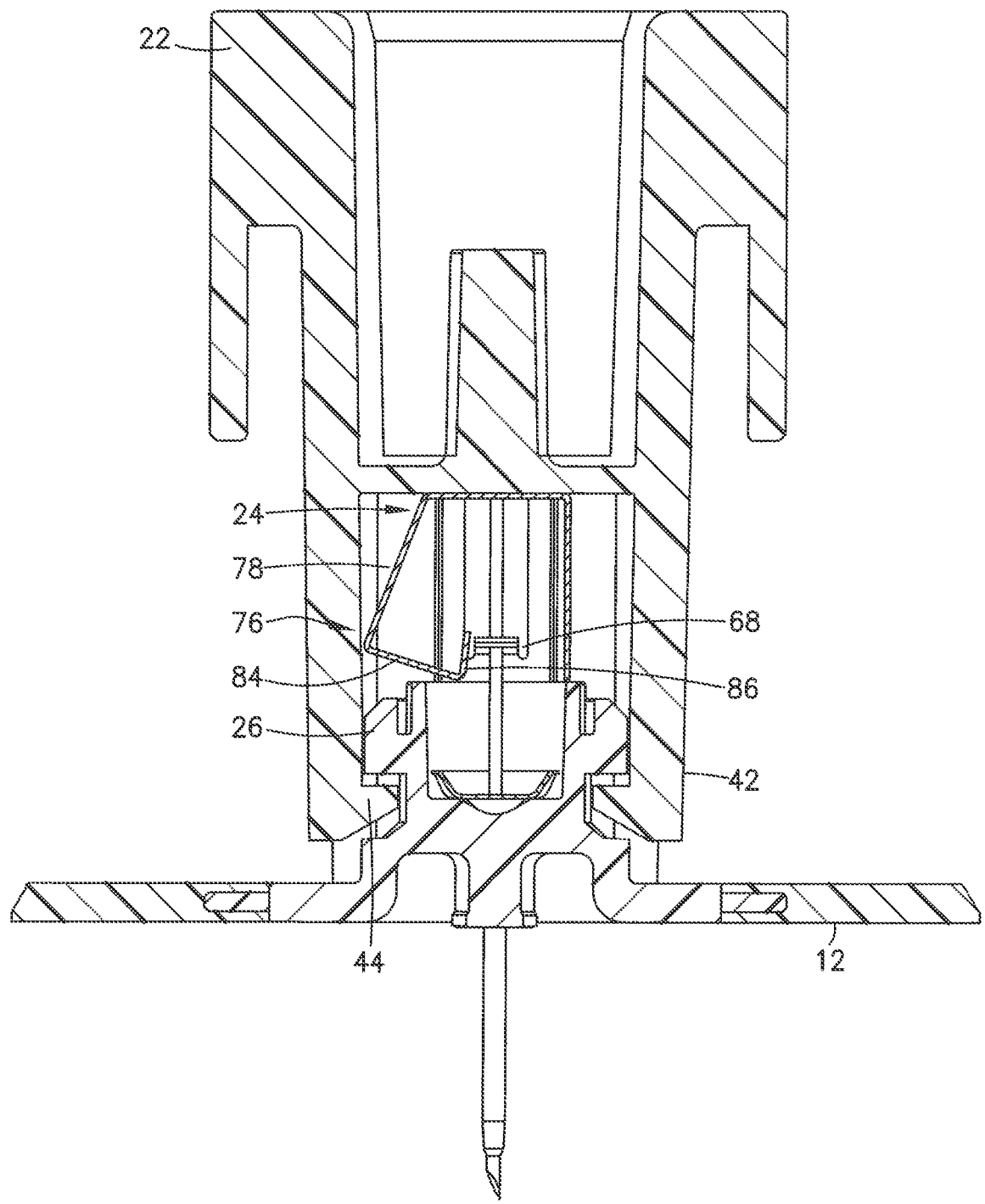
FIG. 5 is a cross-sectional front view of the needle hub assembly of FIG. 3 showing the spring guard contacting the arms of the needle shield.
Figure 8:
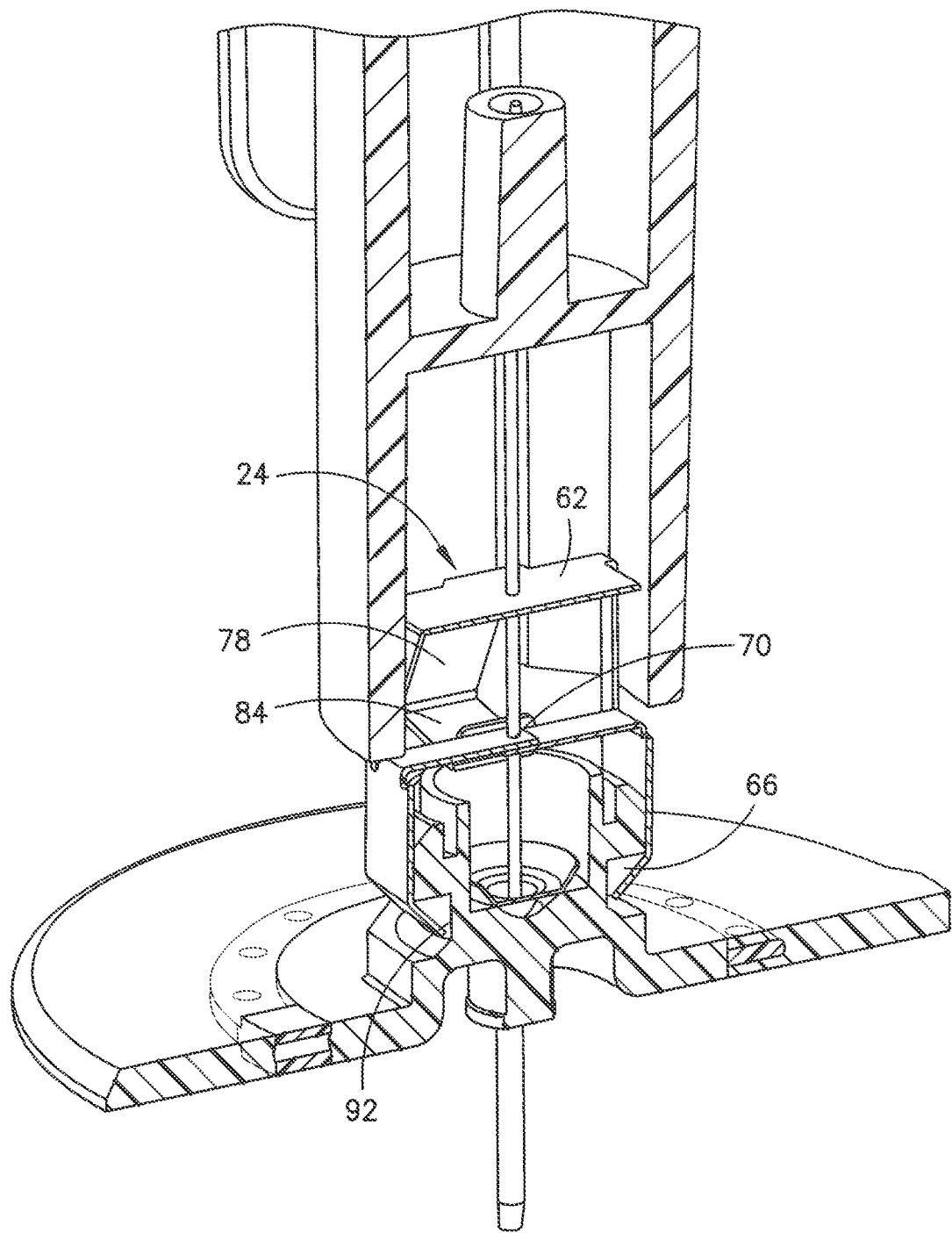
FIG. 8 is a perspective view of the needle hub and needle shield of FIG. 3 showing the needle hub pulled from the needle shield while the introducer needle contacts the arms of the needle shield.

Body 62 of needle shield 24 includes a spring guard 76 integrally formed with body 62 shown in FIG. 5. Spring guard 76 is spring biased inwardly toward the center axis of needle shield 24 and introducer needle 20. Spring guard 76 is formed with a leg 78 having a proximal end 80 extending from body 62 and distal end 82 shown in FIG. 4. As shown in FIG. 8, proximal end 80 includes an end flange 84 extending inwardly at an angle with respect to the center axis of needle shield 24. Flange 84 in the embodiment shown extends at a substantially right angle to the longitudinal dimension of leg 78. An upwardly extending tab 86 extends from the distal end of flange 84 in a direction toward body 62.

Figure 10:
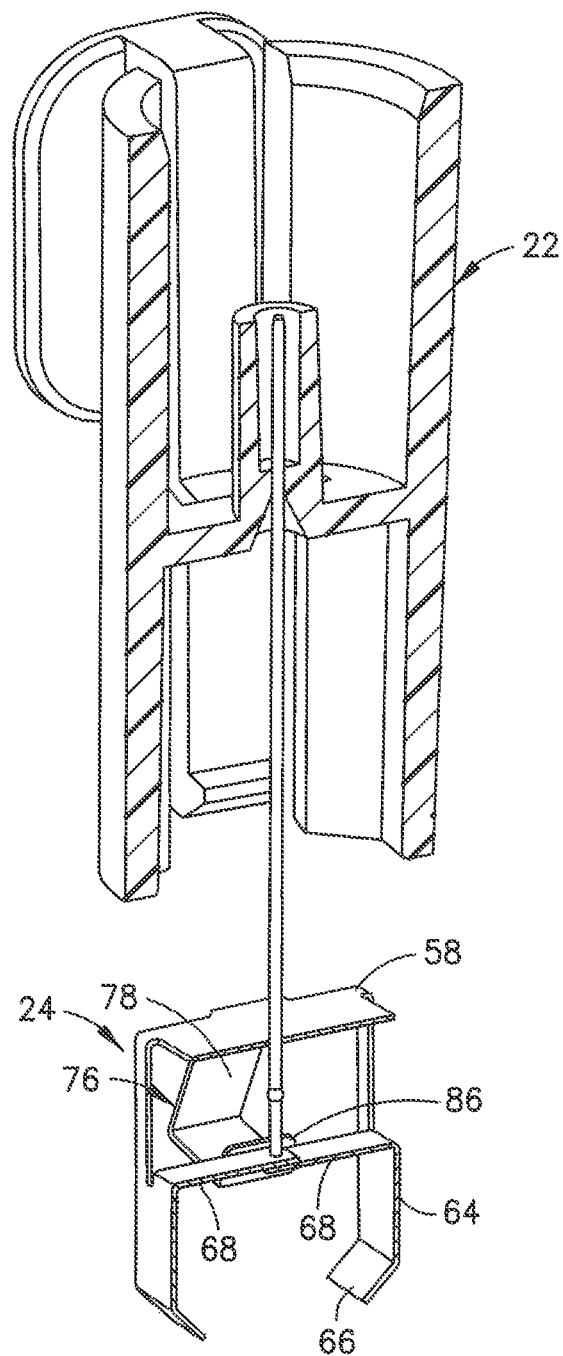
FIG. 10 is cross-sectional view without the base showing the needle shield before being triggered.

Spring guard 76 is spring biased inwardly so that tab 86 is biased toward and contacts inwardly extending arms 68 when introducer needle 24 is received in apertures 70 and arms 68 are retained in the retracted position as shown in FIG. 4. When introducer needle 20 is retracted and withdrawn from apertures 70 in arms 68, arms 68 spring outward and spring guard 76 springs inwardly to the position shown in FIG. 10 where flange 84 extends over the tip of introducer needle 20. Needle shield 24 in one embodiment shown has an axially extending flange 88 forming a stop member for spring guard 76. As shown in FIG. 10, flange 88 extends from body 62 in an axial direction and has a longitudinal length to engage tab 86 when spring guard is deployed.

As shown in FIG. 1, base 12 includes a post 92 surrounding an internal cavity. Mushroom-shaped coupling 26 is disposed at the proximal end of the post 92. An internal passage generally extends through the center of base 12 providing a fluid passageway through base 12. As shown in FIG. 2, the internal cavity of the base 12 receives a retaining wedge and the passage receives catheter 18 for fluid communication with coupling 26 and a fluid delivery device. The wedge has a funnel shape with a hollow center portion that narrows from a broad end to a narrow end. The narrow end of the wedge has a tapered end used to receive a terminal end of catheter 18. Catheter 18 is forced over the narrow end of the wedge and the wedge/catheter assembly is inserted into the internal cavity of base 12.

The flexible characteristics of catheter 18 have a tendency to bunch up within base 12 and therefore, the cavity area has a sufficient size to accommodate excess catheter 18 materials that may accumulate within base 12 during the installation of the catheter onto the wedge.

In one embodiment a pre-slit resilient septum is also retained within the internal cavity of base 12. According to an exemplary embodiment, the septum can be held in place within base 12 by a press fit, which provides a friction force between the septum and both base 12 and the wedge. Alternatively, the septum can be fixed within base 12 by an adhesive or by swaging plastic material from base 12 over the top of the septum, or a combination of the above-described methods. The septum can be made of a soft resilient material including, but not limited to silicones, isoprene rubbers, or bromobutyl rubbers and combinations thereof. The septum ensures a complete seal during infusion and when the fluid connector is disconnected from base 12.

A fluid connector can be connected to coupling 26 of base 12 during use to deliver the drug or medication to the patient. One example of a fluid connector and septum are disclosed in WO 2013/086463 which is incorporated by reference in its entirety.

In each of the herein disclosed embodiments and in other alternative embodiments, the components of the infusion device can be made of injection-molded polypropylene, polyethylene, acrylonitrile butadiene styrene polymers, polyesters such as polyethylene terephthalate or similar materials, and/or bio-based resins such as polylactide, starch-filled polypropylene, or polyhydroxyalkanoates. The catheter can be a separate component or it can be injection-molded as part of the base assembly, either as a single part or as a coinjection-molded part using two resins. Soft shot components can be of ethylene vinyl acetate, thermoplastic urethanes, styrenic thermoplastic elastomers, cellulosic elastomers, copolyester elastomers, or similar materials.

FIGS. 1-10 show the steps and positions for inserting needle hub assembly and catheter 18 into a patient and removing needle hub 20 from base 12 to deploy needle shield 24 over the tip of introducer needle 20. In use, the assembly is inserted into the patient and the user pulls upwardly on insertion device 46 to pull up on needle hub 20 and introducer needle 20. In one embodiment, insertion device 46 is coupled to needle hub 22 by a friction fit so that the upward force of insertion device 46 pulls needle hub 22 upward and retracts introducer needle 20 from coupling 26 of base. The upward force on insertion device 46 and needle hub 22 retracts introducer needle 20 and separates introducer needle 20 from arms 68 of needle shield 24 to allow legs 64 to release from coupling 26 and deploy spring guard 76 over the tip of introducer needle 20.

FIG. 1 is an exploded view showing needle hub 22 in cross section. FIG. 2 is a cross sectional view of needle hub assembly 10 where latching tabs 66 of needle shield 24 are connected to coupling 26 of base 12. The bottom end of needle hub 22 contacts base 12 in a position for introducer needle 20 and catheter 18 to penetrate the skin of the patient. Insertion device 46 is positioned over needle hub assembly 10 and base 12 to assist in applying an insertion force to introducer needle 20 and catheter 18. Needle hub assembly 10 in the position shown in FIG. 2 is assembled for use to insert introducer needle 20 and catheter 18 into the patient.

Figure 3:
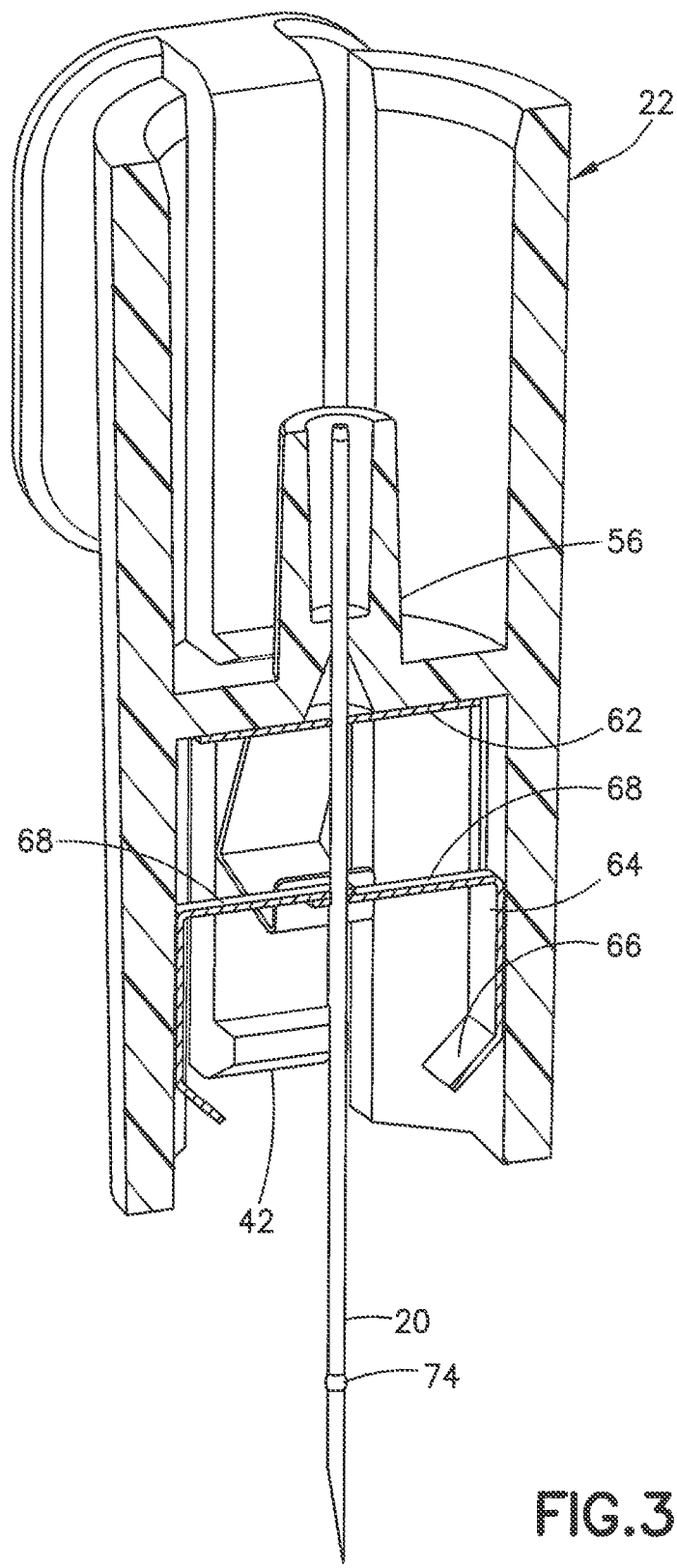
FIG. 3 is a cross-sectional view of the needle hub assembly without the base.

FIG. 3 is an enlarged cross sectional view of the assembly of FIG. 2 showing arms 68 receiving introducer needle 20 to retain legs 64 in a latched position on coupling 26. FIG. 5 is a side cross sectional view of the assembly showing tab 86 of spring guard 76 in contact with arms 68. In the embodiment shown, spring guard and tab 86 do not contact introducer needle 20 in the loaded position shown in FIG. 4 or in the deployed position shown in FIG. 10. In the assembled position of FIG. 4, latching hooks 44 of needle hub 22 are engaged with undercut 30 of coupling 26 of base 12. FIG. 5 is a perspective view in cross section of hub assembly 10 of FIG. 5 showing latching tabs 66 of needle shield connected to coupling 26.

Figure 6:
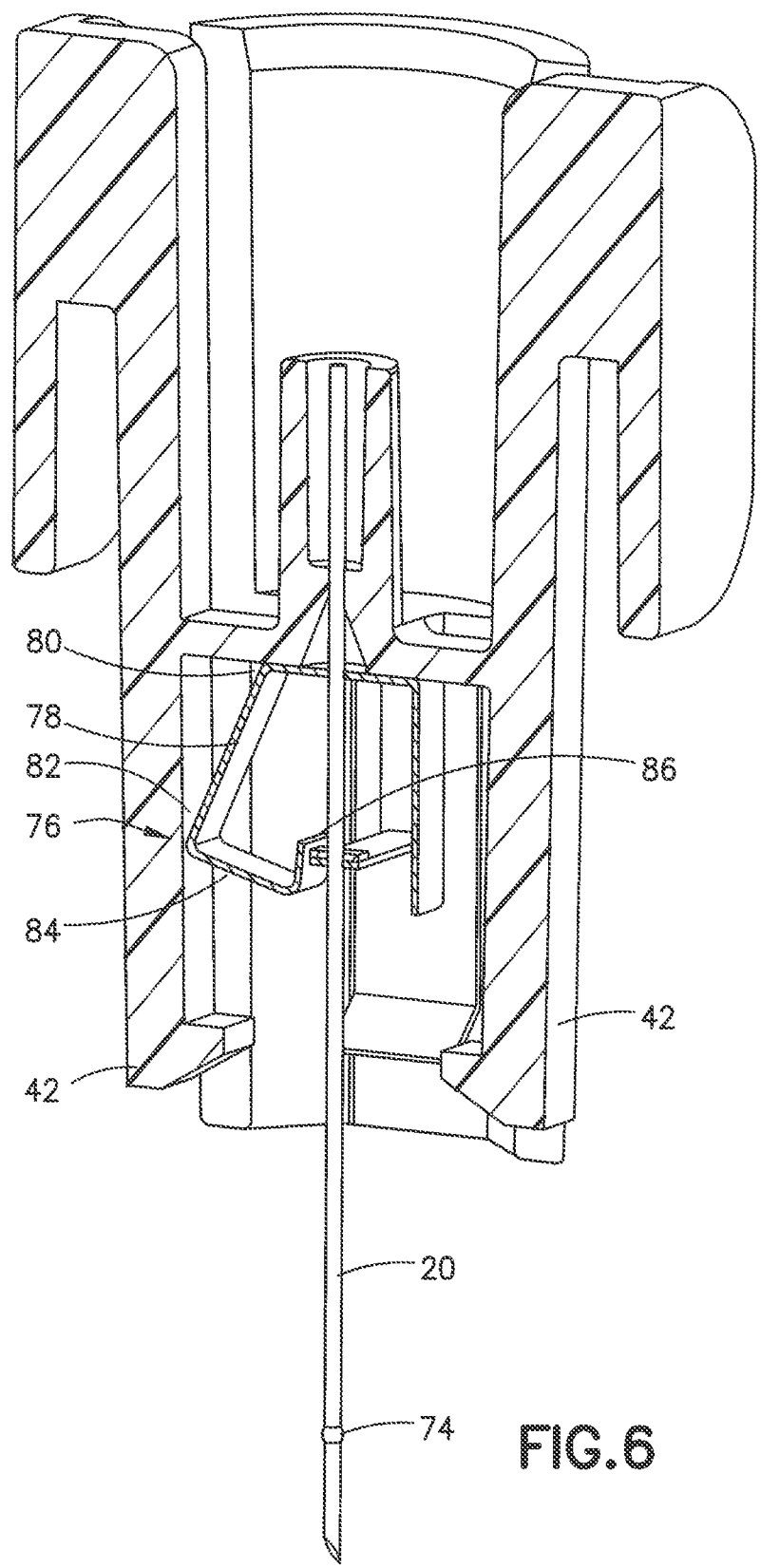
FIG. 6 is a cross-sectional view showing the spring guard contacting the arms without the base.
Figure 7:
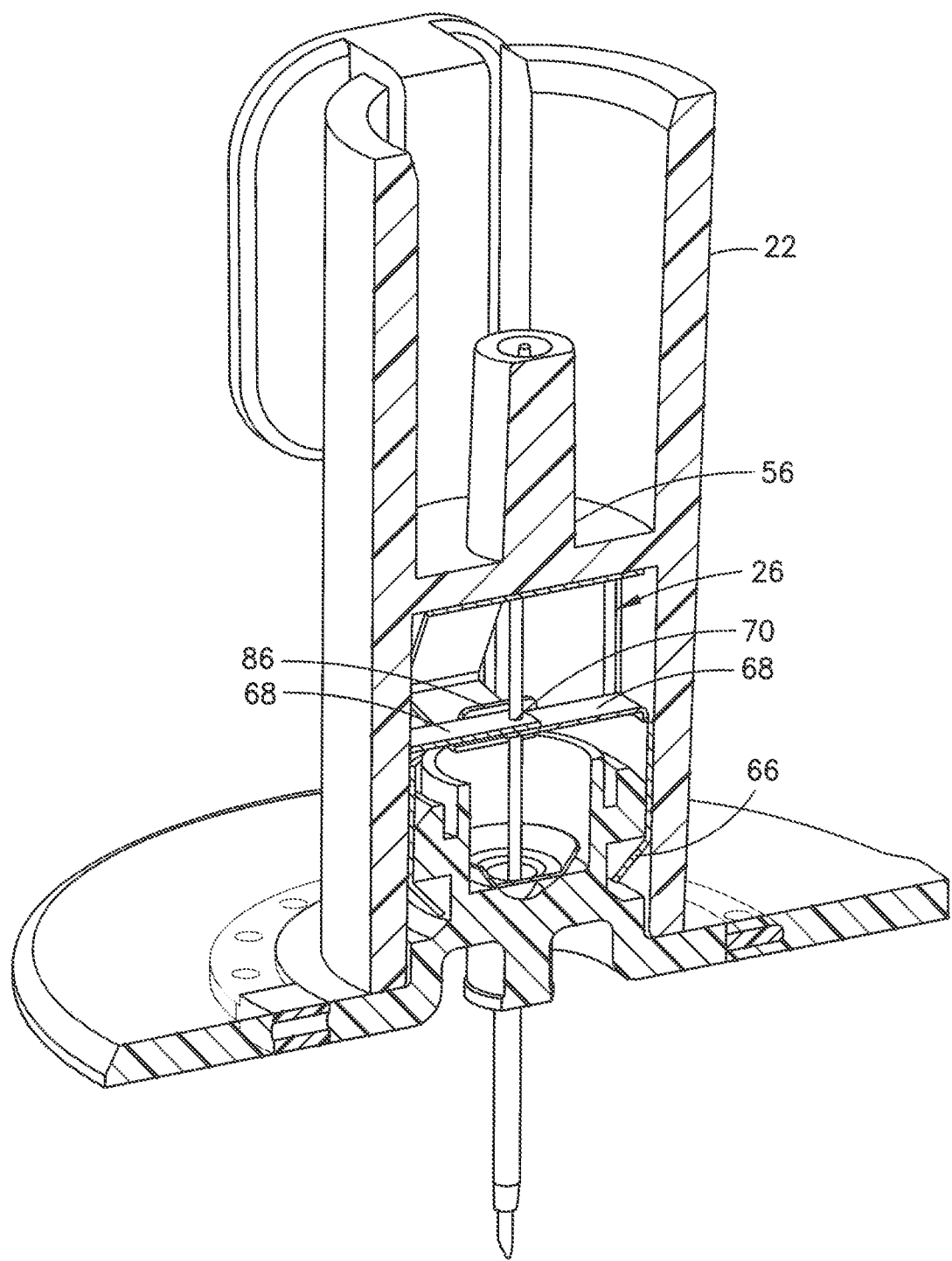
FIG. 7 is a perspective view in cross section of the needle shield and needle hub of FIG. 3.
Figure 11:
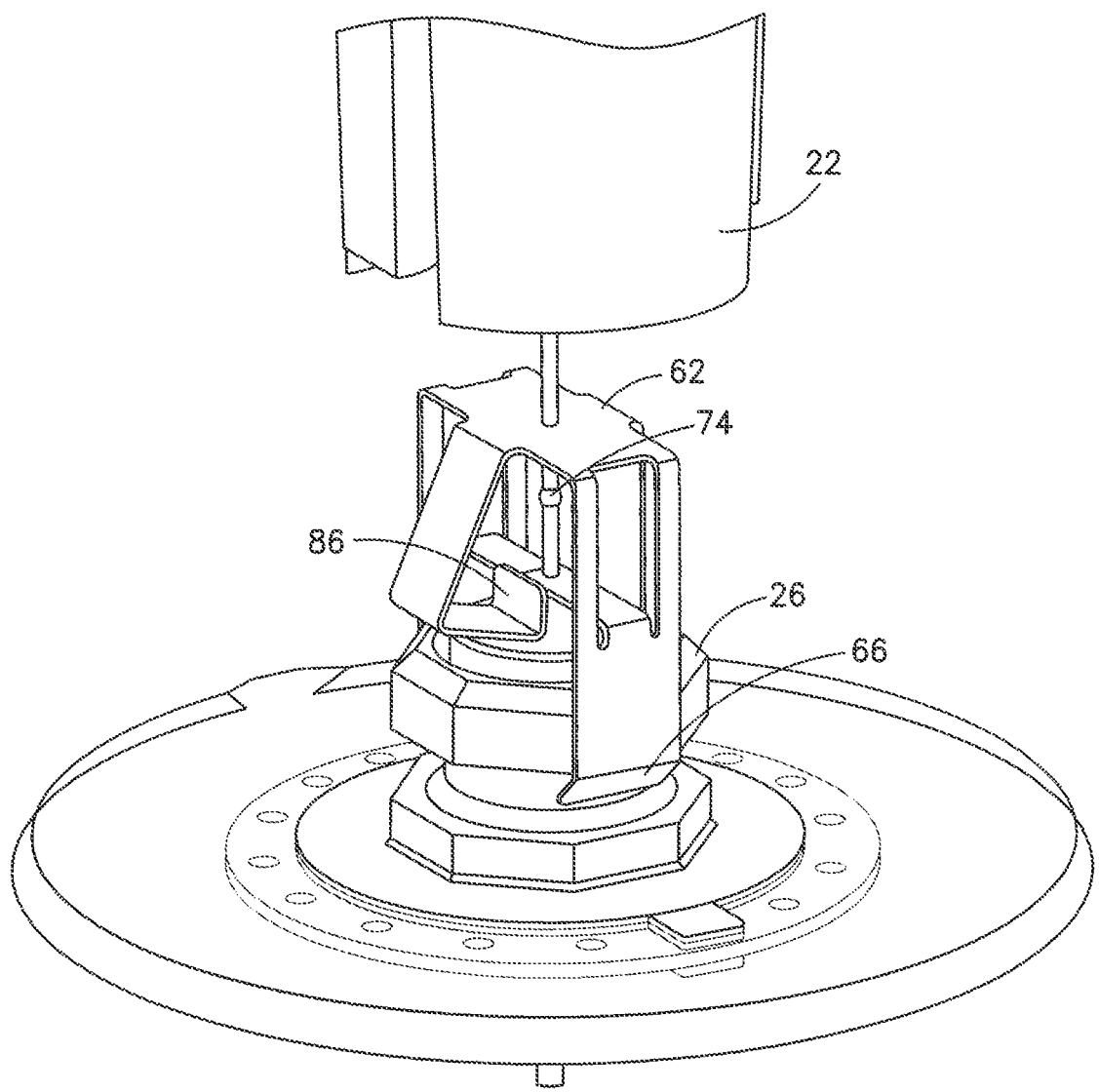
FIG. 11 is a perspective view of the needle hub and needle shield of FIG. 7 showing the spring guard contacting the arms of the needle shield.
Figure 12:
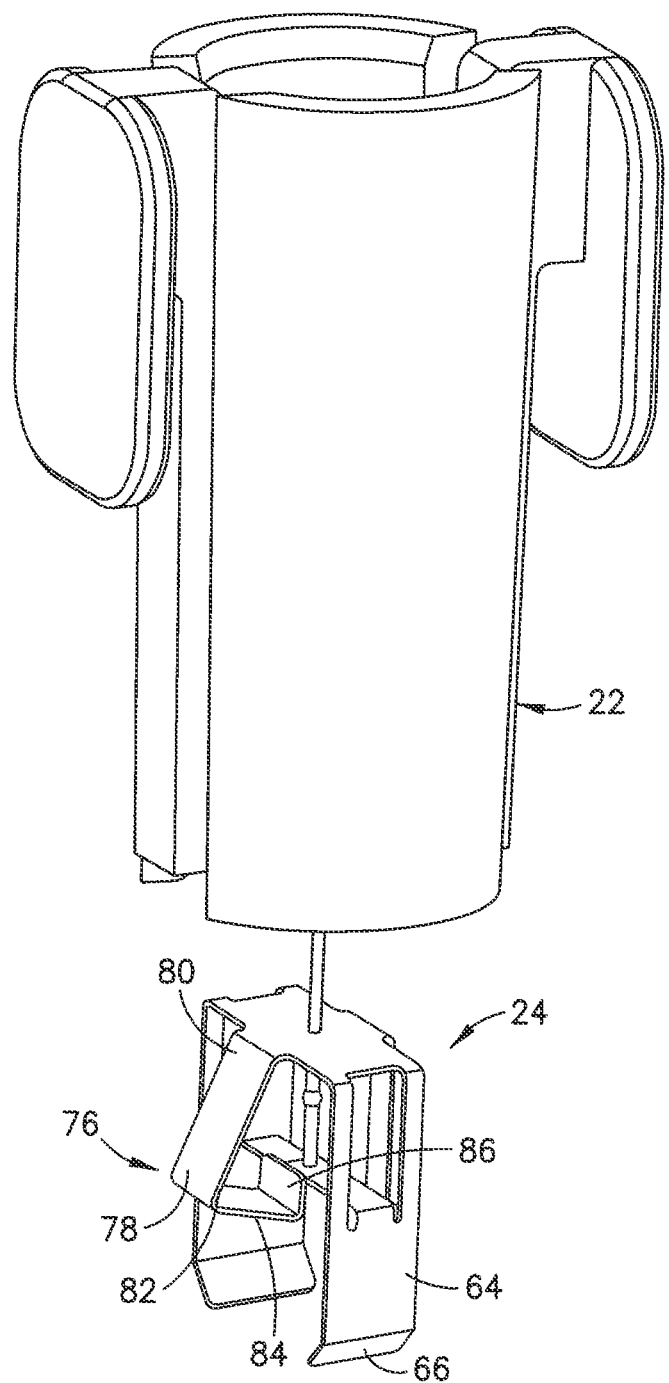
FIG. 12 is perspective view without the base showing the spring guard before being triggered.
Figure 13:
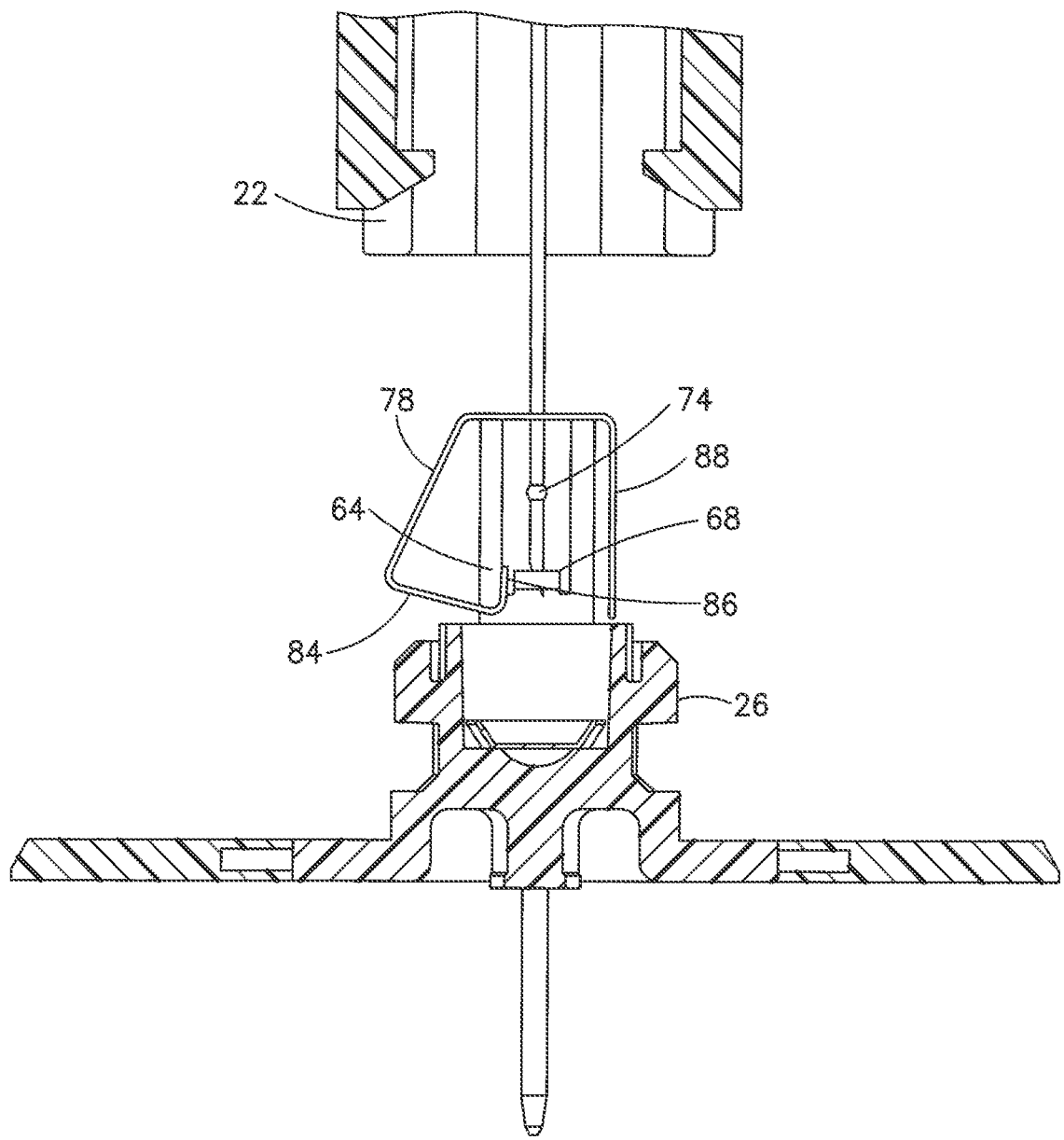
FIG. 13 is a cross-sectional view showing the spring guard of the needle shield contacting the arms of the needle shield.

FIG. 6 is a perspective view of needle hub assembly showing needle hub 22 in the process of retracting introducer needle 20 from catheter 18. In the position shown in FIG. 6, introducer needle 20 is partially withdrawn from catheter 18 and needle shield 24 is partially withdrawn from the open end of needle hub 22 to a position where legs 64 of needle shield 24 are free from needle hub 22. In the position of FIG. 6, introducer needle 20 is still received in apertures 70 of arms 68 of needle shield 22 to retain legs 64 in the loaded position and gripping coupling 26 of base 12. FIG. 8 shows needle hub 22 and introducer needle 20 withdrawn to a further extent than in FIG. 7 where needle shield 24 is completely withdrawn from the open end of needle hub 22 while introducer needle 20 still retains legs 64 in the loaded position by being received in apertures 70. FIG. 8 is a rear view and FIGS. 9 and 10 are front views showing spring guard 72 retained against arms 68. FIGS. 11 and 12 are rear views showing spring guard 72 contacting arms 68.

Figure 14:
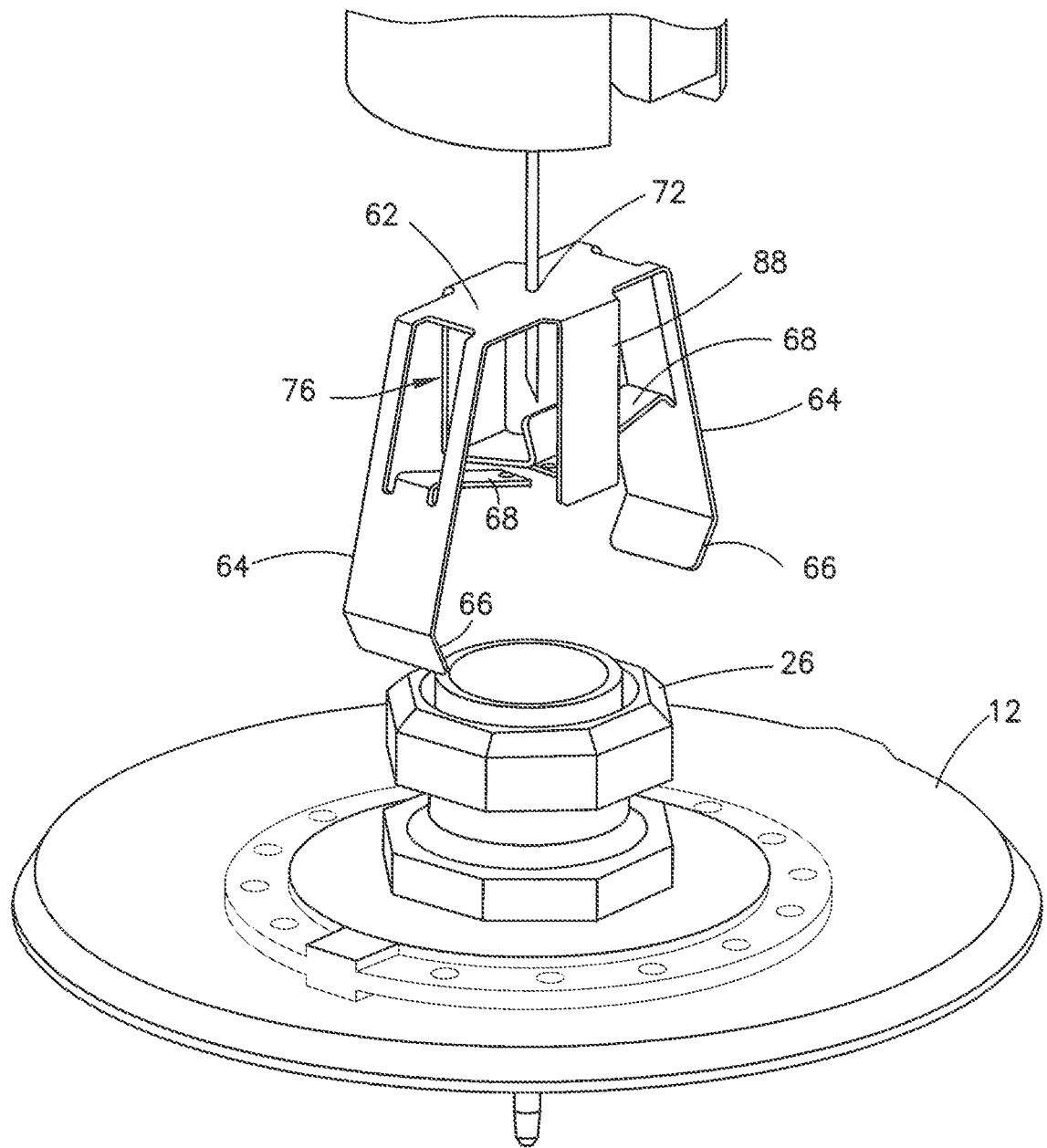
FIG. 14 is a perspective view showing the needle hub and needle shield separated from the base of the infusion device.
Figure 15:
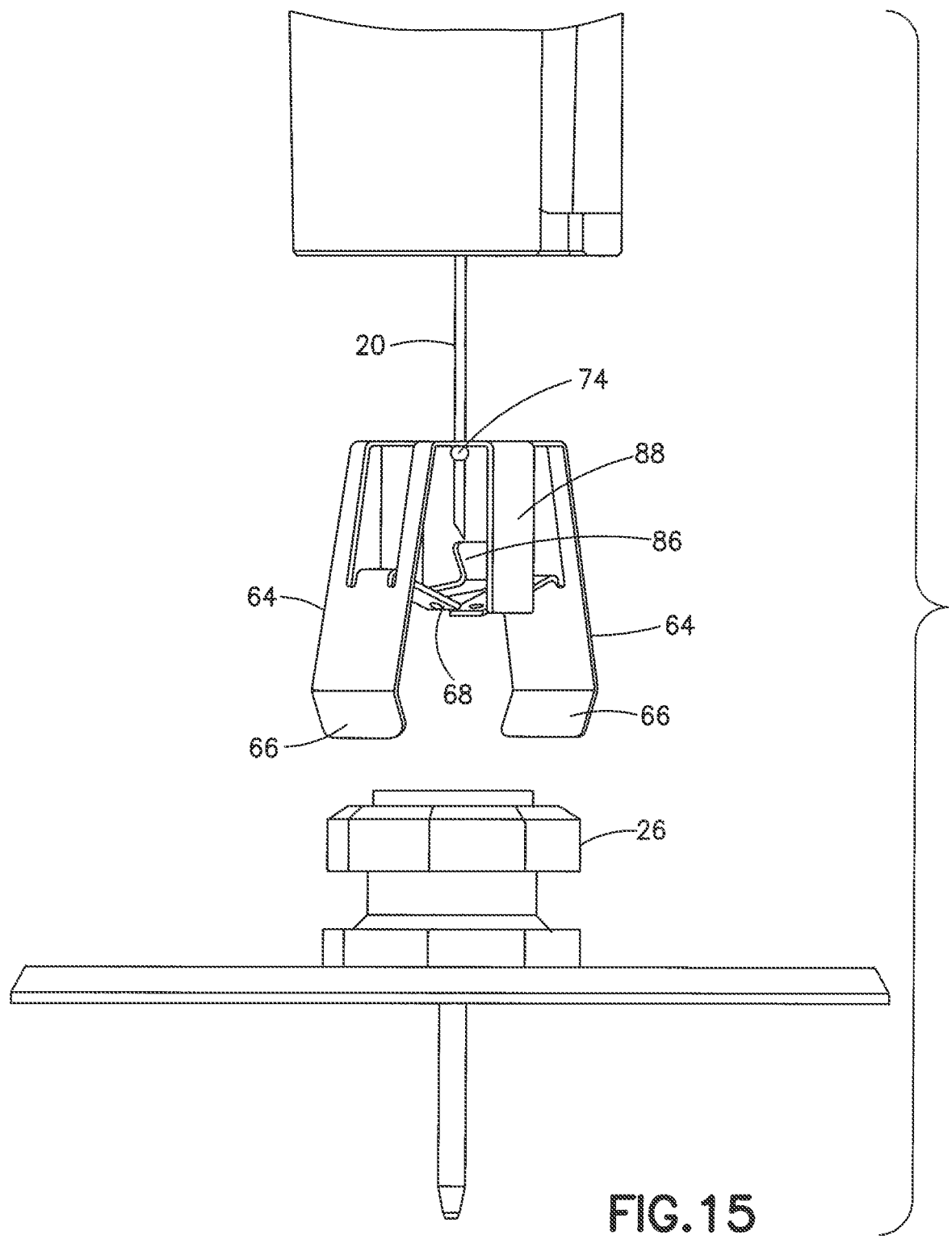
FIG. 15 is a side view showing the needle hub and needle shield separated from the base.
Figure 16:
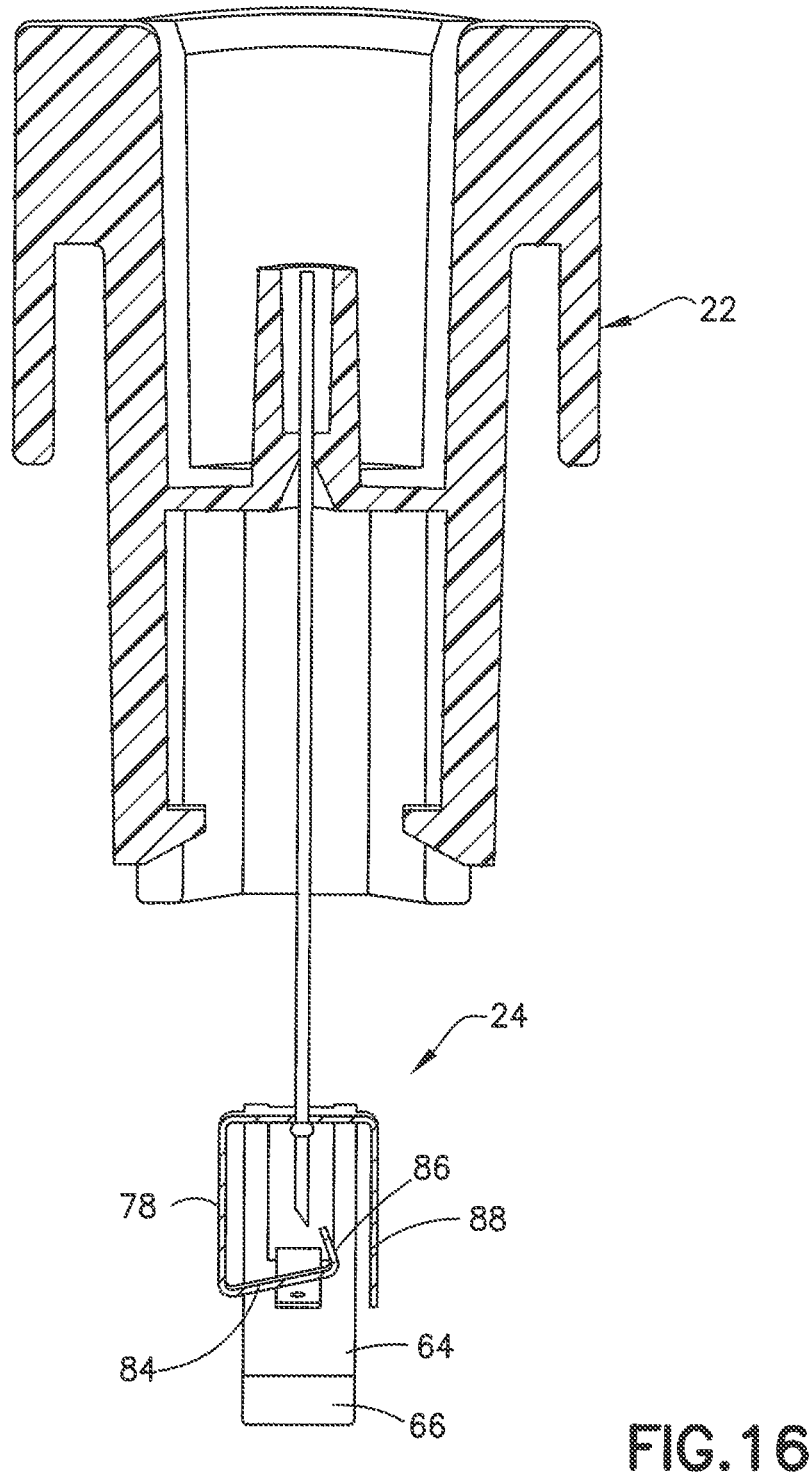
FIG. 16 is a cross-sectional view showing the needle shield in the deployed position.
Figure 17:
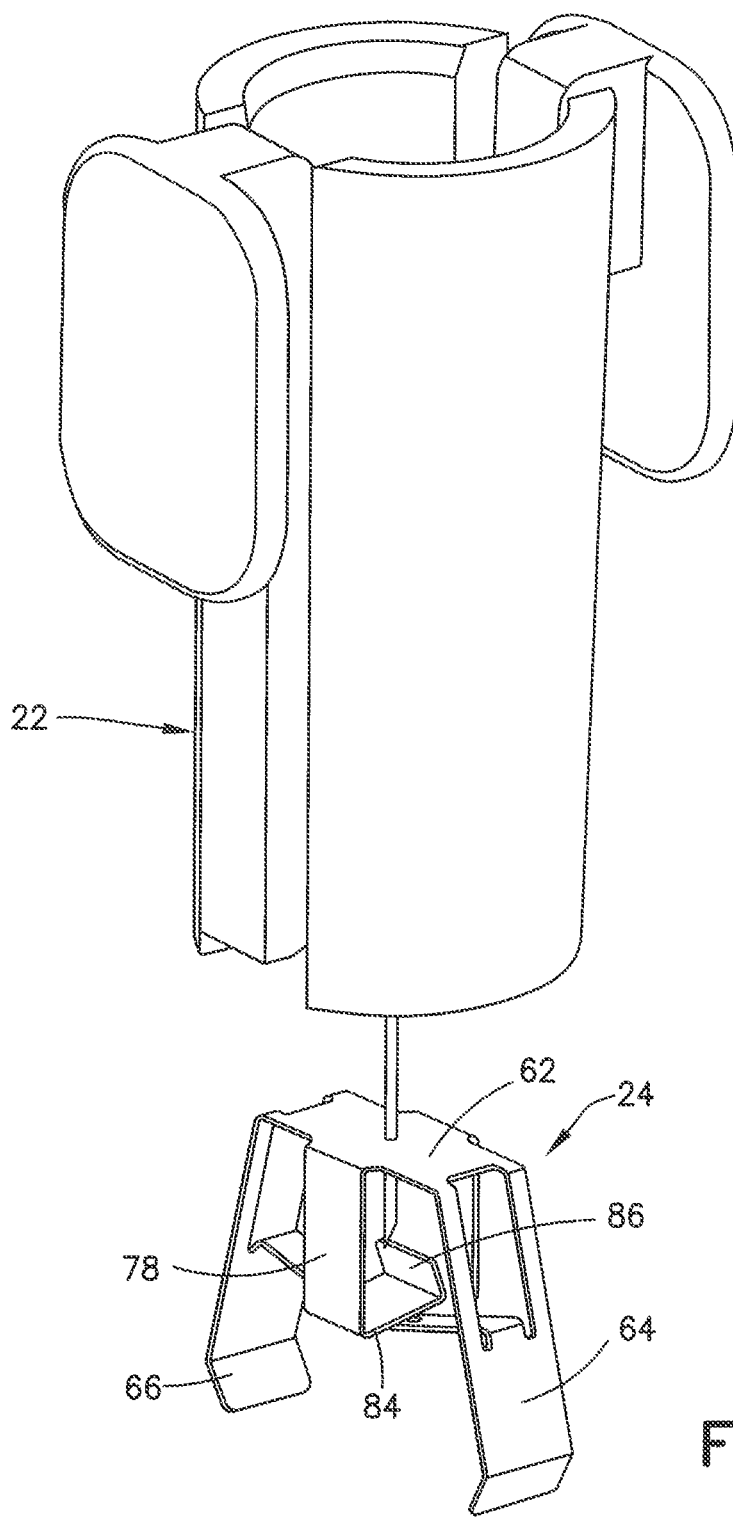
FIG. 17 is a perspective view showing the needle shield in the deployed position.

FIG. 14 is a perspective view showing introducer needle 20 retracted from apertures 70 in arms 68 to allow legs 64 to spring outward and release coupling 26 of hub 12. By legs 64 moving outward, arms 68 also move outward away from tab 86 of spring guard 76 so that spring guard biases inwardly over the tip of introducer needle 20 into contact with stop member 88. Bump 74 contacts a bottom surface of body 62 to prevent separation of needle shield 24 from introducer needle 20. Flange 84 of spring guard 76 is deployed to a position shown in FIG. 10 and FIGS. 14-17 to prevent introducer needle 24 from sliding outward from needle shield 24 and covering the tip of introducer needle 20, thereby reducing the risk of accidental contact with the sharp tip.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the appended claims and their equivalents.

The invention claimed is:

1. An infusion device comprising:
 a base having a catheter and a coupling;
 a needle hub having an introducer needle with a proximal end coupled to said needle hub and a distal end, said introducer needle extending though an axial passage of said catheter; and
 a needle shield slidably received in said needle hub, said needle shield having a proximal end and a distal end, said distal end comprising a leg coupled to said coupling of said base when said introducer needle is in contact with said leg and said leg of said needle shield is received in said needle hub, and when said leg of said needle shield is withdrawn from said needle hub and said introducer needle is withdrawn and separated from said leg, said leg springs outwardly and disengages from said coupling of said base.

2. The infusion device of claim 1, wherein said needle hub is adapted for coupling to an outer surface said coupling of said base, and said leg is coupled to the outer surface of the base.

3. The infusion device of claim 1, further comprising two of said legs, each of said legs having a distal end with an inwardly extending tab for engaging said coupling of said base.

4. The infusion device of claim 3, wherein each of said legs has an inwardly extending arm with an aperture for receiving said introducer needle to retain each of said legs engagement with said coupling of said base.

5. The infusion device of claim 4, where said needle hub has a side wall and an open end receiving said needle shield wherein said side wall contacts each of said legs when said legs are in said needle hub, and where retracting said needle hub and introducer needle with respect to said base separate said introducer needle from said arms and separates said side wall from said legs whereby said legs spring outward from said coupling of said base.

6. The infusion device of claim 5, wherein said needle shield has a spring guard contacting said arms in a first position and said arms move outwardly when each of said legs move outward, whereby said spring guard biases to a second position over the distal end of said introducer needle.

7. The infusion device of claim 6, wherein a body of said needle shield includes an aperture receiving said introducer needle, and where said introducer needle has a bump with an outer diameter greater than an inner diameter of said aperture to prevent separation of said needle shield with respect said introducer needle.

8. The infusion device of claim 5, wherein said needle hub has an inwardly extending hook at said open end for connecting to said coupling of said base.

9. The infusion device of claim 1, wherein said coupling of said base is configured for connecting to a delivery device.

10. The infusion device of claim 1, wherein said needle hub has an open end receiving said needle shield when said needle shield is in a first position, said needle shield being movable to a second position where said leg of said needle shield is not in said needle hub whereby said leg springs outward to separate from said coupling of said base.

11. An infusion device comprising:
 a base having a catheter and a coupling;
 a needle hub having a recess at an open end, and introducer needle positioned within said recess and having a proximal end coupled to said needle hub and a distal end for extending through an axial passage of said catheter;
 a needle shield removably received in said recess of said needle hub, said needle shield having two outwardly biased legs, said legs having a distal end for coupling with said needle hub in a first position and an arm for contacting said introducer needle, and a spring guard biased toward said introducer needle and said arms of said two legs;
 wherein said introducer needle in a first position contacts said arms to retain said two legs in coupling engagement with said needle hub and where said introducer needle is in a second position and said needle shield is withdrawn from said recess of said needle hub, said two legs bias outwardly to a second position to disengage from said needle hub and said spring guard is biased to a position over said distal end of said introducer needle.

12. The infusion device of claim 11, wherein said needle hub has an inwardly extending hook at said open end for connecting to said coupling of said base, and said distal end of said two legs have an inwardly extending tab for connecting to said base, and said distal end of said two legs have an inwardly extending tab for connecting to said coupling of said base.

13. The infusion device of claim 12, wherein said arms have an aperture receiving said introducer needle to retain said two legs in said first position.

14. The infusion device of claim 13, wherein said introducer needle has a bump with an outer dimension greater than an inner dimension of said aperture in said arms to retain said needle shield on said introducer needle.

15. The infusion device of claim 11, wherein said needle hub has a side wall defining said open end, and where said side wall contacts said two legs when said two legs are in said first position, and where retracting said needle hub and introducer needle with respect to said base separates said introducer needle from said two legs and separates said side wall from said two legs whereby said two legs spring outward to said second position.

16. The infusion device of claim 15, wherein said side wall includes an inwardly extending hook at said open end for connecting to said coupling of said base, and said distal end of said two legs have an inwardly extending tab for connecting to said coupling of said base.

17. The infusion device of claim 11, wherein said coupling of said base is configured for connecting to a delivery device.

18. A needle hub assembly comprising:
a needle hub having an introducer needle with a proximal end coupled to said needle hub and a distal end, said introducer needle configured for extending through a catheter of an infusion device;
a needle shield having a proximal end and a distal end, said distal end comprising two legs biased away from each other, each leg having an arm contacting said introducer needle, and a spring guard configured to flex between a first position and a second position biased in a direction toward a longitudinal axis of said introducer needle;
wherein when said distal end of said introducer needle engages said legs, said spring guard contacts said legs and is retained in said first position, and when said introducer needle is withdrawn to disengage from said legs, said spring guard is biased to said second position over said distal end of said introducer needle.

19. The needle hub assembly of claim 18, wherein said needle hub has a side wall and an open end, and where said needle shield is movable between a first position received in said open end of said needle hub and a second position separated from said needle hub.

20. The needle hub assembly of claim 19, wherein said open end of said needle hub includes an inwardly extending hook configured for connecting to a coupling of an infusion device base, and said legs have a distal end with an inwardly extending tab for connecting to a coupling of the infusion device base.

21. The infusion device of claim 20, wherein said side wall contacts said legs to retain said legs in said first position when said needle shield is received in said needle hub and where said legs spring outward when said needle shield is in said second position.

22. The needle hub assembly of claim 20, wherein said coupling of said infusion device base is configured for connecting to a delivery device.

* * * * *